(12) United States Patent
Enquist et al.

(10) Patent No.: US 10,352,848 B2
(45) Date of Patent: Jul. 16, 2019

(54) GAS DETECTION USING GAS MODULATION

(71) Applicant: INFICON GmbH, Bad Ragaz (CH)

(72) Inventors: Fredrik Enquist, Linkoping (SE);
Niclas Edvardsson, Linkoping (SE);
Johan Hellgren, Linkoping (SE);
Henrik Vennerberg, Linkoping (SE)

(73) Assignee: INFICON GmbH, Bad Ragaz (CH)

( * ) Notice: Subject to any disclaimer, the term of this patent is extended or adjusted under 35 U.S.C. 154(b) by 0 days.

(21) Appl. No.: 15/771,640

(22) PCT Filed: Oct. 24, 2016

(86) PCT No.: PCT/EP2016/075560
§ 371 (c)(1),
(2) Date: Apr. 27, 2018

(87) PCT Pub. No.: WO2017/072076
PCT Pub. Date: May 4, 2017

(65) Prior Publication Data
US 2018/0313749 A1  Nov. 1, 2018

(30) Foreign Application Priority Data
Oct. 29, 2015  (EP) ..................... 15192115

(51) Int. Cl.
*G01T 1/18* (2006.01)
*G01N 21/3504* (2014.01)
*G01N 21/03* (2006.01)
*G01N 21/39* (2006.01)
*G01N 33/00* (2006.01)
*G01N 21/17* (2006.01)

(52) U.S. Cl.
CPC ....... *G01N 21/3504* (2013.01); *G01N 21/031* (2013.01); *G01N 21/1717* (2013.01); *G01N 21/39* (2013.01); *G01N 33/0016* (2013.01); *G01N 33/0026* (2013.01); *G01N 2021/1723* (2013.01); *G01N 2201/0698* (2013.01)

(58) Field of Classification Search
CPC .......... G01N 21/3504; G01N 21/1717; G01N 33/0016; G01N 33/0026; G01N 2021/1723; G01N 21/39; G01N 21/031; G01N 2201/0698
See application file for complete search history.

(56) References Cited

U.S. PATENT DOCUMENTS

| | | | |
|---|---|---|---|
| 2,965,842 A * | 12/1960 | Jacobson | H01L 29/00 257/414 |
| 7,030,381 B2 | 4/2006 | Kilian et al. | |
| 2004/0051043 A1 | 3/2004 | Kilian et al. | |
| 2007/0167853 A1 * | 7/2007 | Melker | A61B 5/082 600/532 |
| 2008/0231719 A1 * | 9/2008 | Benson | G01J 5/061 348/222.1 |
| 2011/0077545 A1 | 3/2011 | Eichler | |

* cited by examiner

*Primary Examiner* — Kiho Kim
(74) *Attorney, Agent, or Firm* — The Webb Law Firm

(57) ABSTRACT

A gas detection system, comprising a sample gas inlet, a reference gas inlet and a gas modulation valve alternatingly connecting one of the sample gas inlet and the reference gas inlet to a gas sensor, is characterized in that a selective transfer filter is located in the gas flow path connecting the gas modulation valve and the gas sensor.

12 Claims, 2 Drawing Sheets

GAS DETECTION USING GAS MODULATION

CROSS-REFERENCE TO RELATED APPLICATIONS

This application is the United States national phase of International Application No. PCT/EP2016/0755060 filed Oct. 24, 2016, and claims priority to European Patent Application No. 15192115.2 filed Oct. 29, 2015, the disclosures of which are hereby incorporated in their entirety by reference.

BACKROUND OF THE INVENTION

Field of the Invention

The invention refers to a gas detection system and to a respective method using a gas modulation valve switching between a reference gas inlet and a sample gas inlet.

Description of Related Art

Such a gas modulation valve and respective gas modulation is described in U.S. Pat. No. 7,030,381 B2, the contents of which are incorporated herein by reference. Gas detectors according to U.S. Pat. No. 7,030,381 B2 may comprise a sample gas inlet through which the gas to be detected (target gas) is sucked and a reference gas inlet through which gas from the surrounding atmosphere is sucked as a reference gas. The gas modulation valve connects the sample gas inlet and the reference gas inlet to the inlet of a gas sensor, such as an infrared gas sensor.

The infrared gas sensor may, for example, have a cuvette comprising the inlet and a respective outlet for the gas to be analyzed, an infrared light source and an infrared detector. The gas flow path from the gas modulation valve to the inlet of the gas sensor (cuvette) is alternately connected to the sample gas inlet and to the reference gas inlet by the gas modulation valve. The switching by the gas modulation valve between the sample gas inlet and the reference gas inlet preferably occurs in a periodical manner at a periodic frequency, as described in U.S. Pat. No. 7,030,381 B2.

Regulations throughout the world require regular survey of gas networks to check for possible leakage. The reason for this is primarily to protect the public from fires and explosions resulting from gas collecting in buildings and other confined spaces. The leak survey is typically carried out by moving a detector, sensitive to one of the main components of the gas, over the surface of the ground above the pipe carrying the gas.

The majority of detectors for this purpose utilize only one inlet and no secondary reference inlet.

A typical infrared sensor often used in this type of detector is a non-dispersive infrared absorption detector (NDIR sensor). Another sensor type which might be used for gas detection according to the gas modulation principle is a metal oxide semi-conductor sensor, such as an $SnO_2$ sensor. Both the NDIR and MOS sensors suffer from limited selectivity versus water vapour. When walking with a hand-held probe, it is therefore a common problem that the gas sensor reacts when e.g. moving from an asphalt surface onto a grass surface with a higher humidity or from a sunny area into a shady area or vice versa. Similar selectivity problems are observed on most types of gas sensors. The invention is therefore not meant to be restricted to a specific sensor type.

Various filters are known to be used for removing or capturing the humidity and/or non-wanted flammable gases from the gas sample. The filters need to have a large enough capacity to last for an acceptable amount of time. The filter needs to be replaced, baked out or otherwise regenerated quite often.

SUMMARY OF THE INVENTION

It is an object of the invention to improve the selectivity for a gas detector of the gas modulation type without the need for regular filter replacement.

According to a non-limiting embodiment of the invention, the gas detection system of the invention comprises a sample gas inlet, a reference gas inlet and a gas modulation valve alternatingly connecting one of the sample gas inlet and the reference gas inlet to a gas sensor. The system is characterized by a selective transfer filter located in the gas flow path connecting the gas modulation valve and the gas sensor, and may be acting as a low-pass filter for gases of no interest that cause unwanted signals in the system. The most common of such gases is water or humidity.

The term "selective transfer filter" means that different gas components or gas types are selectively transferred through the filter with different transfer times. Thereby, the gas transfer time of specific gas components is controlled in order to achieve a selectivity of the filter for specific gas components via the respective transfer time of this gas component compared to other gas components. The selective transfer filter may achieve different transfer times for different gas types or components, for example, via a different time behavior of the filter for adsorption and desorption of respective gases or gas species resulting in specific transfer times or passage times of different gas species through the filter. The different transfer times may be expressed by the filtering time constant of the filter for respective gases or species. The selective transfer filter may thus also be named "retention filter" or "physical low-pass filter".

The filtering time constant of the selective transfer filter for disturbing species, i.e. unwanted gases or humidity, should be significantly longer, preferably more than five times longer, than the filtering time constant for the target gas or gases and the period of the switching of the gas modulation valve between the sample gas inlet and the reference gas inlet.

In particular, the selective transfer filter may be a humidity and/or gas filter. The filter may comprise or be made of at least one of a surface-active material, a cigarette filter material, active carbon material and/or silica gel.

The gas sensor may be an infrared sensor, and preferably a non-dispersive infrared sensor, optically tuned to detect methane, ethane, propane, butane or LPG gases. The gas sensor may be a combination of a non-dispersive infrared (NDIR) sensor and at least one further gas sensor, such as a metal oxide semiconductor (MOS) sensor.

According to non-limiting embodiment of the invention, the method of the invention for gas detection uses a gas detection system as described above and according to any one of the claims. According to the invention, the gas modulation valve alternatingly connects the reference gas inlet and the sample gas inlet with the gas flow path leading to the gas via the selective transfer filter. The filter is used as a low-pass filter to slow down the changes in, for example, the humidity of the gas when switching between the sample gas inlet and the reference gas inlet. In particular, the capacity of the filter does not need to be large enough in order to dry the gas, i.e. reduce the humidity of the gas. Only the changes in humidity during the switching cycles need to be dampened.

The general idea is to employ a selective transfer filter, such as a humidity filter, not for removing or capturing the entire humidity from the gas sample, but rather as a low-pass filter in the gas flow path between the gas modulation valve and the gas sensor. The capacity of the humidity filter only needs to be large enough to dampen changes in humidity when the gas modulation valve switches between the sample gas inlet and the reference gas inlet. Typically, the sample gas inlet sucks in humid gas, e.g. when approaching humid ground surfaces, such as grass. The reference gas inlet at the same time does not suck in the same amount of humidity because the reference gas inlet is located to take up gas from the surroundings of the measuring location, that may contain a test gas background that is to be taken into consideration when detecting the test gas taken up at the measuring location by the sample gas inlet. The humidity filter is not used to dry the gas. The low-pass filter effect of the humidity filter only occurs in combination with the gas modulation valve switching between humid gas and reference gas of less humidity.

Humidity is only an example of a gas or gas property which is affected by the selective transfer filter when passing therethrough. Humidity is hereby considered as a gas component the transfer time of which is significantly increased by the selective transfer filter as compared to a target gas. In the example of a humidity filter, the filter thus has a different (significantly longer) time constant for the "gas" humidity than for the target gas, thereby acting as a low-pass filter for the disturbing gas species humidity. If the analyzed gas is a mixture of a possible target gas and other gas components different from humidity but still unwanted, the selective transfer filter may be adapted to achieve a longer transfer time for those unwanted gas components than for the target gas. The longer transfer time may be achieved through a larger filtering time constant.

BRIEF DESCRIPTION OF THE DRAWINGS

In the following, an embodiment of the invention is discussed with reference to the figures.

DESCRIPTION OF THE INVENTION

Figure 1:
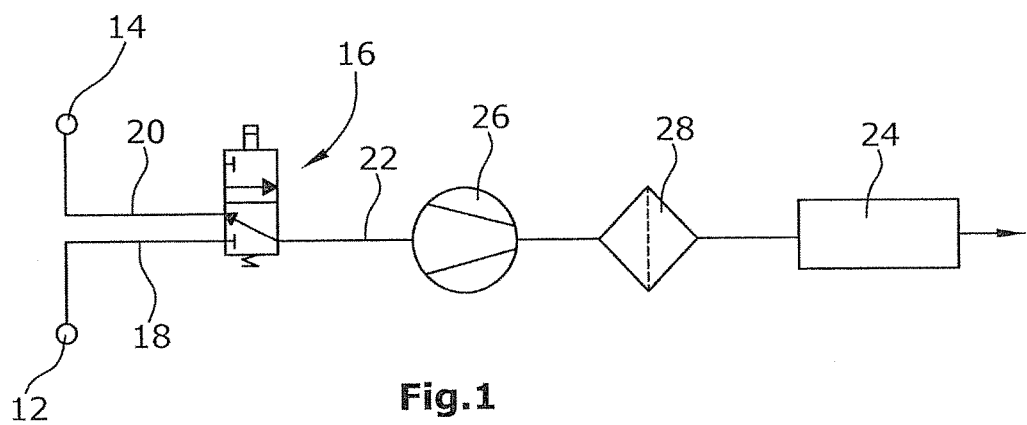
FIG. 1 shows the general layout of the system of the invention.

A sample gas inlet 12 and a reference gas inlet 14 are connected to a gas modulation valve 16 via respective sample and reference gas conduits 18, 20. The gas modulation valve 16 alternatingly connects the sample gas conduit 18 or the reference gas conduit 20 to the gas flow path 22 connecting the gas modulation valve 16 and the gas sensor 24. In the embodiment shown in FIG. 1, the gas sensor 24 may be a non-dispersive infrared sensor comprising an absorption cuvette. The gas flow path 22 contains a sample vacuum pump 26 and a selective transfer filter 28. The selective transfer filter 28 is located between the gas modulation valve 16 and the gas sensor 24. The selective transfer filter 28 is also located between the vacuum pump 26 and the gas sensor 24. The vacuum pump 26 is located between the gas modulation valve 16 and the filter 28.

The gas modulation valve 16 is opened and closed in a cyclic manner, thereby alternatingly and periodically connecting the sample gas inlet 12 or the reference gas inlet 14 to the gas flow path 22. The switching occurs at a frequency suitable for the application, depending on the signal update frequency demanded by the application and/or the time constant of the gas detection sensor 24. The selected frequency is typically a compromise between application demands (typically a few hertz or higher) and the time constant of the gas sensor 24 which, in reality, is seconds or minutes for most sensor types.

The gas modulation valve 16 is used to create a signal modulation for noise reduction and signal amplification. Thereby, the valve 16 takes gas from the sample gas inlet 12 at the actual point of interest or the reference gas inlet 14 from the background air in an alternating cycle. The output signal of the gas sensor 24 is analyzed in relation to the switching frequency and sometimes also the phase in order to improve the sensitivity and to reduce background noise.

An increase in humidity in the ambient air will be suppressed because both the sample gas inlet 12 and the reference gas inlet 14 take gas from the ambient air. Non-gas related noise will also be suppressed as this will normally not coincide with the gas signal in frequency and phase.

The major problem with the prior art systems employing gas modulation switching between a sample gas inlet and a reference gas inlet is that ambient conditions may be changing differently between the separated gas inlets. This occurs, for example, when the ground surface is screened with a hand-held probe for gas emerging from underground pipes. This is often done by dragging a carpet-like device on the surface. The sample inlet is then typically placed below the carpet and the reference gas inlet is placed above the carpet. Accordingly, when the carpet is moved between areas of different humidity, there will be an immediate difference in humidity of the sample gas and the reference gas entering the sample gas inlet 12 and the reference gas inlet 14, respectively. This difference in humidity between the sample gas and the reference gas will result in a signal with the same frequency as the modulation and can, therefore, not be adequately suppressed by filtering algorithms. This is at least the case when the humidity difference is large enough to induce a signal in the gas sensor 24.

The selective transfer filter 28 between the gas modulation valve 16 and the gas sensor 24 is a surface-active humidity filter. The filter 28, through which a continuous flow of air is passing, does not need to have the capacity to remove all of the humidity from the sample. It is rather enough that the filter 28 slows down the changes in humidity due to the gas modulation, thereby acting as a humidity low-pass filter. The time constant of the filter is significantly larger than the time period of the gas modulation cycle. Thereby, the humidity level after the filter will eventually adapt to the average of humidity in the sample gas and the reference gas, but, as the time constant is significantly longer than the gas modulation cycle, this can be suppressed by the signal algorithms.

Typical filter materials, such as surface-active filter materials, cigarette filter materials, activated carbon material or silica gel not only slow down humidity changes, but also changes in concentration of heavier hydrocarbons or other flammable gases. This invention therefore works best for detection of light gases such as hydrogen and methane when employing conventional surfaces active filtering materials. Using chemically tailored filters it would, however, also be possible to implement this invention for the other gases.

Hydrocarbons typically influence most gas sensors including infrared sensors such as the NDIR sensor. Other flammable gases typically influence most general gas sensors but to a lesser extent NDIR sensors.

The sensor 24 needs to have a large enough differential sensitivity for the target gas to be detected in the actual average humidity or average gas concentration in the ambient atmosphere. For example, the gas sensor 24 may be specified to detect 1 ppm methane. The gas detection system can work in a background of 50 ppm methane, if the sensing system can distinguish 51 ppm from 50 ppm. The same applies for humidity and other interfering gases.

Figure 2:
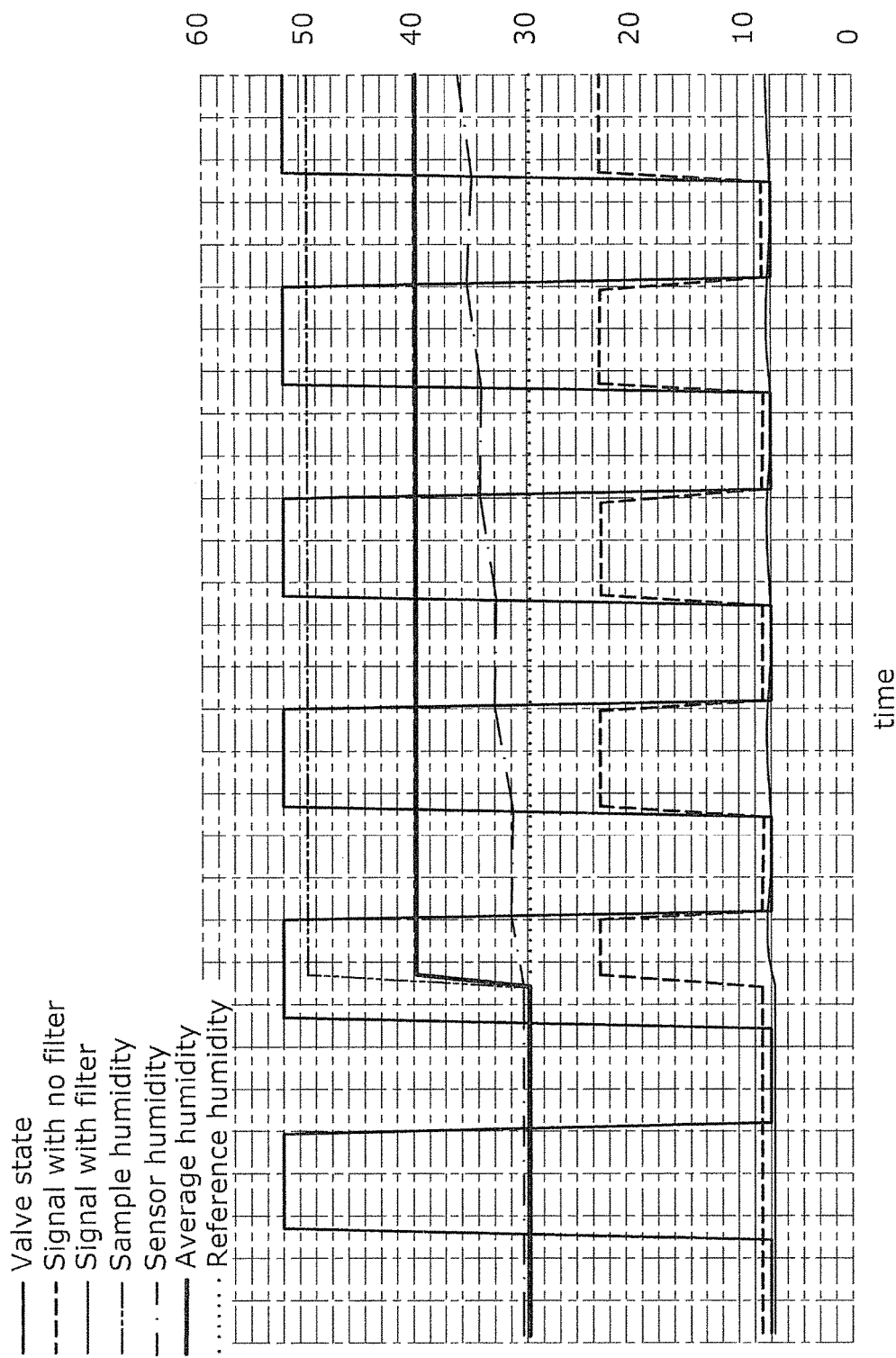
FIG. 2 shows humidity percentage over time in an embodiment employing a humidity filter.

FIG. 2 shows different kinds of measurement signals (without filter and with filter) and respective humidity when the gas modulation valve 16 switches between a sample gas having a larger humidity than the reference gas.

When the sample gas inlet 12 approaches a humid surface, the humidity of the sample gas increases during the cycle, when the gas modulation valve 16 is switched to the sample gas inlet 12. The measurement signal without the filter 28 would increase accordingly during the cycle when the valve 16 is switched to the sample gas inlet 12, and would decrease when the valve 16 is switched to the reference gas inlet 14.

With the selective transfer filter 28, the measurement signal of the gas sensor 24 remains at an almost constant low level with only slight increases during the cycle where the gas modulation valve 16 switches to the sample gas inlet 12.

The invention claimed is:

1. A gas detection system comprising a sample gas inlet, a reference gas inlet, a gas modulation valve alternatingly connecting one of the sample gas inlet and the reference gas inlet to a gas sensor, and
a selective transfer filter located in a gas flow path connecting the gas modulation valve and the gas sensor, the selective transfer filter adapted to selectively transfer different gas components or gas types with different time constants.

2. The gas detection system according to claim 1, wherein the selective transfer filter has a filtering time constant for disturbing gas species that is significantly longer than a filtering time constant for a target gas and a period of switching the gas modulation valve between the sample gas inlet and the reference gas inlet.

3. The gas detection system according to claim 2, wherein the selective transfer filter has a filtering time constant for disturbing gas species that is more than five times longer than the filtering time constant for the target gas and the period of switching the gas modulation valve between the sample gas inlet and the reference gas inlet.

4. The gas detection system according to claim 1, wherein said selective transfer filter comprises at least one of a surface-active material, a cigarette filter material, an active carbon material, and a silica gel.

5. The gas detection system according to claim 1, wherein said gas sensor is an infrared sensor optically tuned to detect methane, ethane, propane, butane, or LPG gases.

6. The gas detection system according to claim 5, wherein said gas sensor is a non-dispersive infrared sensor.

7. The gas detection system according to claim 1, wherein the gas sensor is a combination of a non-dispersive infrared sensor and at least one further gas sensor.

8. A method for gas detection using a gas detection system according to claim 1, the method comprising alternatingly connecting said gas modulation valve to the reference gas inlet and the sample gas inlet with the gas flow path leading to the gas sensor via the selective transfer filter.

9. The method according to claim 8, wherein a filtering time constant of the selective transfer filter is significantly longer than a filtering time constant for a target gas and a period of the gas modulation.

10. The method according to claim 9, wherein the filtering time constant of the selective transfer filter is more than five times longer than the filtering time constant for the target gas and the period of gas modulation.

11. The method according to claim 8, wherein the selective transfer filter is used as a low-pass filter to slow down changes in specific properties of a target gas when switching between the sample gas inlet and the reference gas inlet.

12. The method according to claim 11, wherein the selective transfer filter is used as a low-pass filter to slow down changes in humidity of the target gas when switching between the sample gas inlet and the reference gas inlet.

* * * * *

UNITED STATES PATENT AND TRADEMARK OFFICE
CERTIFICATE OF CORRECTION

PATENT NO. : 10,352,848 B2
APPLICATION NO. : 15/771640
DATED : July 16, 2019
INVENTOR(S) : Fredrik Enquist et al.

Page 1 of 1

It is certified that error appears in the above-identified patent and that said Letters Patent is hereby corrected as shown below:

In the Specification

Column 1, Line 8, delete "PCT/EP2016/0755060" and insert -- PCT/EP2016/075560 --

Signed and Sealed this
Eighth Day of October, 2019

Andrei Iancu
*Director of the United States Patent and Trademark Office*